United States Patent
Pennemann et al.

(10) Patent No.: US 10,041,921 B2
(45) Date of Patent: Aug. 7, 2018

(54) DEVICE AND METHOD FOR PRODUCING AROMATIC AMINES

(71) Applicant: Covestro Deutschland AG, Leverkusen (DE)

(72) Inventors: Bernd Pennemann, Bergish Gladbach (DE); Bodo Temme, Dormagen (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 721 days.

(21) Appl. No.: 14/159,512

(22) Filed: Jan. 21, 2014

(65) Prior Publication Data

US 2014/0206089 A1    Jul. 24, 2014

(30) Foreign Application Priority Data

Jan. 22, 2013   (EP) .................................. 13152196

(51) Int. Cl.
*G01N 33/00*      (2006.01)
*C07C 209/36*     (2006.01)

(52) U.S. Cl.
CPC ....... *G01N 33/0073* (2013.01); *C07C 209/36* (2013.01); *Y10T 436/12* (2015.01)

(58) Field of Classification Search
CPC .................................................. G01N 33/0073
USPC ............................................. 422/62; 436/55
See application file for complete search history.

(56) References Cited

U.S. PATENT DOCUMENTS

| | | | | |
|---|---|---|---|---|
| 2,734,089 A | * | 2/1956 | Starr ..................... | C07C 29/141 568/880 |
| 3,270,057 A | * | 8/1966 | Cooke et al. ......... | C07C 209/36 564/420 |
| 3,497,449 A | * | 2/1970 | Urban ................... | C10G 35/24 208/108 |
| 3,499,034 A | * | 3/1970 | Gonzalez ............. | C07C 209/36 502/185 |

(Continued)

FOREIGN PATENT DOCUMENTS

| | | |
|---|---|---|
| DE | 2 044 657 | 3/1972 |
| DE | 10 2005 008 613 A1 | 8/2006 |

(Continued)

OTHER PUBLICATIONS

Willeboordse, F. et al, Analytical Chemistry 1968, 40, 1455-1458.*

(Continued)

*Primary Examiner* — Arlen Soderquist
(74) *Attorney, Agent, or Firm* — Donald R. Palladino

(57) ABSTRACT

The invention relates to a method for producing organic amino compounds from organic nitro compounds, wherein the organic nitro compound hydrogenated to the organic amino compound with a hydrogen-containing gas stream by means of a catalyst, the reaction course of the hydrogenation being monitored by analysis of secondary products forming during hydrogenation, wherein the method is characterized in that the concentration of one or more gaseous secondary products is determined in the gas phase and if the concentration falls below a predefinable minimum concentration the hydrogenating activity of the catalyst is increased. The present invention also relates to a device for performing said method.

15 Claims, 1 Drawing Sheet

(56) References Cited

U.S. PATENT DOCUMENTS

| | | | | |
|---|---|---|---|---|
| 3,654,131 A * | 4/1972 | Carr | ............... | B01J 19/0006 208/143 |
| 3,729,512 A * | 4/1973 | L'Eplattenier et al. | ............... | H01L 29/74 556/136 |
| 3,754,125 A * | 8/1973 | Rothstein | ............... | C07C 209/36 422/108 |
| 3,755,550 A * | 8/1973 | Stiles | ............... | C01B 17/0478 423/244.02 |
| 3,972,804 A * | 8/1976 | McLaughlin | ............... | C10G 49/26 208/108 |
| 3,972,946 A * | 8/1976 | Ochiai | ............... | B01J 19/0006 568/449 |
| 4,071,572 A * | 1/1978 | Amato | ............... | C07C 17/156 570/243 |
| 4,219,679 A * | 8/1980 | Onopchenko | ............... | B01J 27/043 564/418 |
| 4,476,094 A * | 10/1984 | Carson | ............... | C10G 49/26 408/DIG. 1 |
| 4,536,276 A * | 8/1985 | Carson | ............... | C10G 49/26 208/100 |
| 5,093,535 A * | 3/1992 | Harrison | ............... | B01J 8/02 554/141 |
| 5,283,365 A * | 2/1994 | Nagata | ............... | C07C 209/36 564/423 |
| 5,399,742 A * | 3/1995 | Tennant | ............... | C07C 67/303 560/127 |
| 5,616,806 A * | 4/1997 | Nagata | ............... | C07C 209/36 564/423 |
| 6,005,143 A * | 12/1999 | Machado | ............... | B01J 19/2465 564/420 |
| 6,156,933 A * | 12/2000 | Poliakoff | ............... | B01J 3/008 564/416 |
| 6,179,996 B1 * | 1/2001 | Baker | ............... | C10G 49/007 208/100 |
| 6,327,521 B1 * | 12/2001 | Prober | ............... | B01J 19/0006 525/355 |
| 6,350,911 B1 * | 2/2002 | Sander | ............... | B01J 4/002 564/305 |
| 6,548,305 B1 * | 4/2003 | Deves | ............... | G01N 31/10 422/130 |
| 7,091,383 B2 | 8/2006 | Vanoppen et al. | | |
| 7,323,597 B2 * | 1/2008 | Hugo | ............... | C07C 209/48 564/336 |
| 7,339,080 B2 * | 3/2008 | Hugo | ............... | C07C 209/48 564/415 |
| 7,453,012 B2 * | 11/2008 | Bocquenet | ............... | C07C 209/48 564/490 |
| 7,511,176 B2 * | 3/2009 | Pohl | ............... | C07C 209/36 564/420 |
| 7,595,424 B2 * | 9/2009 | Vanoppen | ............... | B01J 8/006 564/420 |
| 7,626,057 B2 * | 12/2009 | Kumano | ............... | C07C 209/48 564/385 |
| 8,071,389 B2 * | 12/2011 | Weck | ............... | B01J 8/067 436/144 |
| 8,575,404 B2 * | 11/2013 | Jevtic | ............... | C07C 29/149 568/885 |
| 8,895,783 B2 * | 11/2014 | Raichle | ............... | C07C 209/36 564/420 |
| 9,139,510 B2 * | 9/2015 | Merkel | ............... | C07C 209/36 |
| 9,150,493 B2 * | 10/2015 | Lorenz | ............... | C07C 209/36 |
| 2001/0051844 A1 * | 12/2001 | Prober | ............... | B01J 19/0006 700/269 |
| 2002/0094681 A1 * | 7/2002 | Armbrust | ............... | C23C 16/52 438/680 |
| 2003/0157003 A1 * | 8/2003 | Machado | ............... | B01J 3/04 422/242 |
| 2004/0073066 A1 | 4/2004 | Zehner et al. | | |
| 2004/0202573 A1 * | 10/2004 | van den Brink | ............... | B01J 19/0046 506/38 |
| 2004/0260487 A1 * | 12/2004 | Evans | ............... | B01J 8/0015 702/50 |
| 2006/0258889 A1 * | 11/2006 | Hugo | ............... | C07C 209/48 564/415 |
| 2007/0017291 A1 * | 1/2007 | Cypes | ............... | B01D 3/00 73/590 |
| 2007/0021586 A1 * | 1/2007 | Marrow | ............... | B01J 19/0006 528/363 |
| 2007/0027345 A1 * | 2/2007 | Hugo | ............... | C07C 209/48 564/420 |
| 2007/0161829 A1 * | 7/2007 | Van Driessche | ............... | C07C 11/02 568/883 |
| 2008/0009654 A1 * | 1/2008 | Kumano | ............... | C07C 209/48 564/305 |
| 2008/0027248 A1 * | 1/2008 | Peterson | ............... | C07C 45/50 568/454 |
| 2008/0146847 A1 * | 6/2008 | Pohl | ............... | C07C 209/36 564/419 |
| 2008/0146848 A1 * | 6/2008 | Vanoppen | ............... | B01J 8/006 564/420 |
| 2008/0166816 A1 * | 7/2008 | Weck | ............... | B01J 8/067 436/144 |
| 2009/0005598 A1 * | 1/2009 | Hassan | ............... | C07C 209/36 564/420 |
| 2009/0011515 A1 * | 1/2009 | Soleta | ............... | C07F 9/3813 436/104 |
| 2009/0046285 A1 * | 2/2009 | Kang | ............... | G01N 21/031 356/311 |
| 2009/0234165 A1 * | 9/2009 | Chiu | ............... | C07C 17/23 570/136 |
| 2010/0160674 A1 * | 6/2010 | Biskup | ............... | C07C 263/10 560/347 |
| 2011/0137083 A1 * | 6/2011 | Pfeffinger | ............... | B01J 4/002 564/450 |
| 2011/0275858 A1 * | 11/2011 | Coelho Tsou | ............... | C07C 209/36 564/422 |
| 2011/0295039 A1 * | 12/2011 | Raichle | ............... | C07C 209/36 564/421 |
| 2012/0010441 A1 * | 1/2012 | Jevtic | ............... | C07C 29/149 568/885 |
| 2012/0215029 A1 * | 8/2012 | Haase | ............... | C07C 209/34 564/420 |
| 2012/0238779 A1 * | 9/2012 | Waters | ............... | B01J 8/226 564/420 |
| 2012/0289745 A1 * | 11/2012 | Lorenz | ............... | C07C 209/36 564/305 |
| 2013/0006018 A1 * | 1/2013 | Mitchell | ............... | C07C 209/36 564/420 |
| 2013/0211141 A1 * | 8/2013 | Raichle | ............... | C07C 209/36 564/420 |
| 2014/0128638 A1 * | 5/2014 | Merkel | ............... | C07C 209/36 564/423 |

FOREIGN PATENT DOCUMENTS

| | | |
|---|---|---|
| EP | 0 223 035 B1 | 11/1989 |
| WO | 03/066571 A1 | 8/2003 |
| WO | 2011/086050 A2 | 7/2011 |
| WO | 2012/076449 A1 | 6/2012 |

OTHER PUBLICATIONS

Westerterp. K. R. et al, Chemical Engineering and Processing 1997, 36, 17-27.*

McMullen, J. P. et al, Angewandte Chemie International Edition 2010, 49, 7076-7080.*

Bourne, R. A. et al, Organic Process Research & Development 2011, 15, 932-938.*

Westerterp, K. R. et al, Chemical Engineering Science 1992, 47, 4179-4189.*

Datsevich, L. B. et al, Applied Catalysis A: General 2004, 261, 143-161.*

Patrick, R. H. et al, AIChE Journal 1995, 41, 649-657.*

Westerterp, K. R. et al, Chemical Engineering and Processing 1997, 36, 17-27.*

(56) References Cited

OTHER PUBLICATIONS

Yeong, K.K. et al, Chemical Engineering Science 2004, 59, 3491-3494.*
Du, Y. et al, Applied Catalysis A: General 2004, 277, 259-264.*
Kreutzer, M. T. et al, Catalysis Today 2005, 105, 421-428.*
Telkar, M. M. et al, Applied Catalysis A: General 2005, 295, 23-30.*
Relvas, J. et al, Catalysis Today 2008, 133-135, 828-835.*
Rahman, A. et al, Catalyst Letters 2008, 123, 264-268.*
Zheng, Y. et al, Catalyst Letters 2008, 124, 268-276.*
Serna, P. et al, Journal of Catalysis 2009, 265, 19-25.*
Abo-Ghander, N. S. et al, Chemical Engineering Science 2010, 65, 3113-3127.*
Wang, J. et al, Industrial & Engineering Chemistry Research 2010, 49, 4664-4669.*
Panda, K. et al, Industrial & Engineering Chemistry Research 2011, 50, 7849-7856.*

* cited by examiner

DEVICE AND METHOD FOR PRODUCING AROMATIC AMINES

CROSS-REFERENCE TO RELATED APPLICATIONS

This application claims the benefit of priority under 35 U.S.C. § 119(a)-(g) of European Patent No. 13152196.5 filed Jan. 22, 2013.

BACKGROUND OF THE INVENTION

The invention relates to a device and a method for producing organic amino compounds from organic nitro compounds, wherein the organic nitro compound is hydrogenated to the organic amino compound with a hydrogen-containing gas stream by means of a catalyst, the reaction course of the hydrogenation being monitored by analysis of secondary products forming during hydrogenation.

The production of organic amino compounds from corresponding nitro compounds is sufficiently known. In the method described in EP 0 223 035 A1 the hydrogenation is performed with the aid of modified Raney nickel catalysts dispersed in the liquid reaction mixture. The catalyst can be separated out of the liquid reaction mixture by filtration or sedimentation and optionally returned to the process.

Furthermore, a method for producing toluylene diamine by hydrogenation of dinitrotoluene at elevated temperature and elevated pressure at one reactor or at two reactors connected in series is known from DE 2044657. High-pressure tubular-flow reactors containing fixed nickel or ruthenium hydrogenating catalysts are proposed as reactors.

Organic amino compounds, in particular diamino or tri-amino compounds, are an important starting substance for the production of organic polyisocyanates, which in turn are needed for polyurethane production. To this end, toluylene diamine (TDA), for example, a commonly used monomer for polyisocyanate production, is produced via a hydrogenation starting from dinitrotoluene. Catalysts are typically used for the hydrogenation, which is performed in the liquid phase. During the course of the production process problems can arise, through insufficient catalyst activity for example, such that an accumulation of dinitrotoluene occurs in the reactor. This accumulation can present a considerable safety risk, since dinitrotoluene can decompose explosively at elevated temperature and in particular in the presence of strong bases. In order to mitigate this safety risk, complete reaction of the dinitrotoluene that is added to the hydrogenating reactor is desired. A number of approaches to this end are known.

WO 03/066571 A1 discloses the performance of the hydrogenation reaction to completion through analysis of the liquid hydrogenation product by gas chromatography.

DE 10 2005 008 613 A1 proposes determining the concentration of nitro and nitroso compounds by UV/VIS absorption spectroscopy methods.

WO 2012/076449 A1 describes a method for producing aromatic amines by hydrogenating nitro aromatics, wherein a chromatographic analysis of the reaction mixture is performed in order to determine the concentration of nitro and nitroso compounds in the reaction mixture.

Furthermore, experienced plant operators can also draw conclusions about the reaction course from the color of the hydrogenation product. In addition, it is known the completeness of the reaction can also be assessed by monitoring the temperature rise in a reaction chamber connected downstream of the actual reactor. An incomplete reaction can moreover also be detected from a deviation of the reaction stoichiometry, specifically by analysing the ratio between hydrogen and dinitrotoluene. These methods are described for example in WO 2011/086050 A2.

However, the measures that have hitherto been known for checking the completeness of the hydrogenation reactions are not satisfactory in every respect.

Thus, some of these methods require complex equipment, while others rely on the experience of the operating staff, which can inevitably lead to mistakes. Other methods, such as determining the temperature rise for example, deliver the required data with a time delay, which is likewise disadvantageous for optimum control of the hydrogenating reactor.

The object of the present invention was therefore to provide a device and a method for producing organic amines by the hydrogenation of corresponding nitro compounds, which method can be implemented with comparatively inexpensive equipment and delivers timely information about the completeness of the hydrogenation reaction. The device and the method should be safe to use and should above all allow a quantitative reaction of the organic nitro compound combined with an optimised yield of organic amino compound.

SUMMARY OF THE INVENTION

The object is achieved by a method for producing organic amino compounds from organic nitro compounds, wherein the organic nitro compound is hydrogenated to the organic amino compound with a hydrogen-containing gas stream by means of a catalyst, the reaction course of the hydrogenation being monitored by analysis of secondary products forming during hydrogenation, wherein the method is characterised in that the concentration of one or more gaseous secondary products is determined in the gas phase and if the concentration of the one or more gaseous secondary products falls below a predefinable minimum concentration the hydrogenating activity of the catalyst is increased. According to the invention hydrogenating activity of the catalyst is understood to mean the ability of the catalyst to catalyse the hydrogenation of organic nitro compounds to organic amino compounds. This hydrogenating activity can be increased by changing one or more reaction parameters (volumetric flow rate of the hydrogen-containing gas stream, amount of organic nitro compound added, pressure, temperature and/or residence time) such that the catalyst present in the reaction chamber catalyses the hydrogenation of the organic nitro compound with an increased activity in comparison to the state prior to changing the parameter(s). Alternatively or in addition, further catalyst can also be added such that the catalyst then present in the reaction chamber, which is a mixture of existing and fresh catalyst, catalyses the hydrogenation of the organic nitro compound with increased activity in comparison to the state prior to adding further catalyst.

BRIEF DESCRIPTION OF THE SEVERAL DRAWINGS

DETAILED DESCRIPTION OF THE PREFERRED EMBODIMENTS

Figure 1:
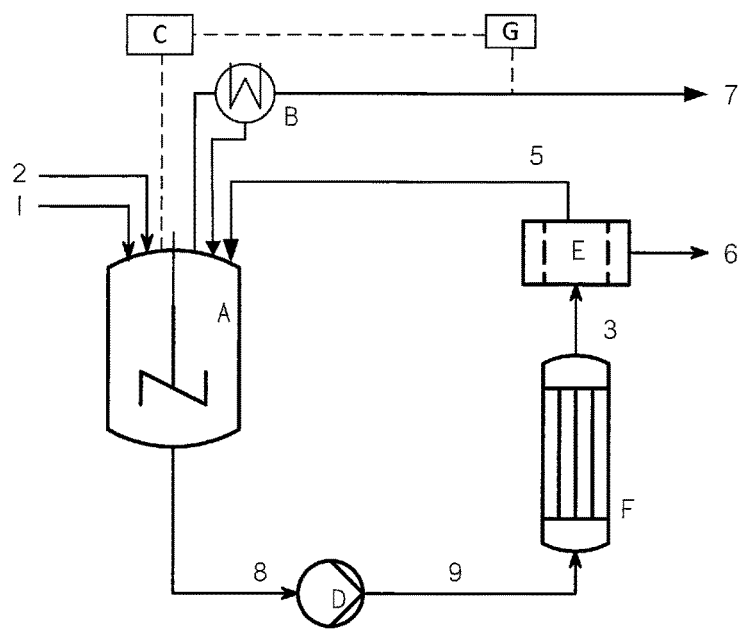
FIG. 1 is a schematic drawing of an embodiment of the process of the present invention.

With the hydrogenation of organic nitro compounds, the amount of hydrogen used in the method according to the invention should be such that the hydrogenation of the nitro compound runs to completion so as to prevent an accumulation of organic nitro compound in the reactor due to unreacted nitro compound, such an accumulation presenting problems in terms of safety. Through the convenient hyper-stoichiometric, use of hydrogen, secondary products are formed in addition to the desired organic amino compound. Thus, with the use of aromatic nitro compounds, for example, ring-hydrogenated amino compounds can also form as secondary products.

The invention is based on the finding that an assertion can be made about the completeness of the hydrogenation reaction from an analysis of secondary products in the gas stream discharged from the hydrogenating reactor. In other words, in the present invention the non-selectivity of the hydrogenation reaction, which in itself is undesirable, is used to ensure that the desired hydrogenation reaction always runs as far as possible to completion, the gaseous secondary product that is analysed advantageously being methane, ammonia and/or an aliphatic amine, which is not itself one of the products, such as methylamine or methylcyclohexylamine.

The hydrogenation of the organic nitro compound to the corresponding amine takes place as a rule with hydrogen or mixtures of hydrogen and inert gases as the hydrogenating reagent. All catalysts conventionally used for catalytic hydrogenations are suitable. Catalysts comprising noble metals such as Pt, Pd, Rh, Ru or non-ferrous metals such as Ni, Co or Cu or mixtures thereof are preferably used. Catalysts comprising Pt, Pd, Ni or Cu are particularly preferably used, generally as a suspension in water. In the case of noble metal catalysts, they are applied to a support such as for example activated carbon, $SiO_2$ or $Al_2O_3$, wherein Raney nickel can also be used in the case of Ni catalysts. The concentration of catalyst in the reaction chamber is preferably 0.01 wt. % to 20 wt. %, preferably 0.5 wt. % to 10 wt. %, relative to the total weight of the reaction mixture in the reaction chamber. Of the suitable catalysts, one is generally chosen that is particularly selective with regard to the target product, which also means that it generates the smallest possible amounts of secondary products. This does not restrict the present invention, but it does mean that a correspondingly low detection limit should be chosen for the secondary products.

If mixtures of hydrogen and inert gases are used, preferred inert gases are ammonia, noble gases and/or nitrogen. Hydrogen or the mixture of hydrogen and inert gases is preferably introduced in such a way that a constant pressure is established in the reaction chamber, i.e. as the reaction progresses (and hence also the hydrogen consumption), the feed of fresh hydrogenating reagent increases. If a mixture of hydrogen and inert gases is used as the hydrogenating reagent, the ratio of hydrogen and inert gas in the hydrogenating reagent feed is gradually increased to prevent a hydrogen depletion in the reactor contents.

In the process according to the invention, hydrogen is preferably used in excess relative to the amount necessary for the hydrogenation of the nitro groups to amino groups. In particular, the hydrogen excess is at least 0.01 mol %, preferably at least 0.1 mol %, relative in each case to the amount of substance necessary for the hydrogenation of the nitro groups to amino groups.

Solvents that are inert under the reaction conditions can optionally be used, such as alcohols such as methanol, propanol, isopropanol, or ethers such as dioxane, tetrahydrofuran. To increase the cost-effectiveness of the method, a low solvent concentration is generally advantageous. Said concentration is conventionally 1 wt. % to 50 wt. %, preferably 20 wt. % to 35 wt. %, relative in each case to the total weight of the liquid phase.

Furthermore, in the method according to the invention, 0.1 to 10 wt. %, preferably 0.2 to 5 wt. % of the hydrogen that is used can be discharged and the concentration of the one or more gaseous secondary products therein can be determined. That is particularly advantageous, since in equipment terms it is less complicated to measure the concentration in this split gas stream than in the product line. Moreover, the accumulation of inert compounds, which for example can be present as traces in the hydrogen feed, can be prevented by this discharge.

The method according to the invention is preferably performed continuously.

According to the invention it is provided that the concentration of the one or more gaseous secondary products is determined in the gas phase. The gaseous secondary products that are analysed preferably have a boiling point under normal pressure of 200° C. or less, in particular of 180° C. or less, more preferably of 80° C. or less, particularly preferably of 50° C. or less, most particularly preferably of 20° C. or less.

The minimum concentration of the one or more gaseous secondary products in the gas phase can vary, depending on the secondary product being analysed. Owing to the variability of the volumetric flow rate that is discharged, in particular of the gaseous hydrogen that is discharged, the minimum concentrations given below relate to the amount of organic nitro compound used. This can be determined for example from the volume concentration of secondary product in the discharged hydrogen, the volumetric flow rate of discharged hydrogen, the pressure, the molar weight of the secondary product and the amount of organic nitro compound added.

The minimum concentration in the case of methane and ammonia is, for example, at least 2 mg/kg of organic nitro compound, preferably 2 to 20 mg/kg, in particular 2 mg/kg, preferably 4 mg/kg, more preferably 10 mg/kg or even 15 mg/kg; in the case of the aliphatic amine it is for example at least 2 mg/kg of organic nitro compound, preferably 1 to 10 mg/kg, in particular 1 mg/kg, preferably 2 mg/kg, more preferably 5 mg/kg or even 7.5 mg/kg. The exact values can depend on catalyst type and reaction conditions and can be further adjusted if required. This can be done for example by selective correlation with one or more of the methods of the prior art for checking the completeness of the reaction. Such methods are known per se to the person skilled in the art. Of the aforementioned secondary products, the determination of methane is particularly advantageous, since this can easily be detected by means of analysis by IR spectroscopy, for example. Methane is formed for example in the hydrogenation reaction of dinitrotoluene by cleavage of the methyl group from the aromatic ring.

All techniques known to the person skilled in the art for determining the concentration of the gaseous secondary product can in principle be used for said purpose in the method according to the invention. A gas chromatograph or gas probe, such as for example a suitable gas electrode, is particularly suitable therefor. By the same token, spectroscopy methods can also be used as an alternative or in addition, in particular a UV/VIS and/or IR spectrometer.

The device for determining the concentration of the gaseous secondary product can in principle be mounted at any suitable point. For example, the device can be connected to a line or arranged in the reactor.

According to a preferred embodiment of the method according to the invention, water vapor present in the gas phase is removed by condensation before determining the concentration of the gaseous secondary product. This is particularly advantageous, since water vapor possibly makes it more difficult to determine the secondary product, particularly in the case of analysis by IR spectroscopy.

It can moreover be provided according to the invention that in the method the gaseous secondary product is passed through a separating apparatus, in particular through a chromatographic column, preferably a GC column, prior to determining the concentration. Possibly disruptive products can be separated off in this way, thereby improving the accuracy of determination of the secondary product used for monitoring the reaction course of the hydrogenation.

The increase in the hydrogenating activity of the catalyst, as provided according to the invention, is performed by increasing the volumetric flow rate of the hydrogen-containing gas stream, by throttling the feed of organic nitro compound, by increasing the pressure, by increasing the temperature, by increasing the residence time and/or by adding further catalyst.

According to a further preferred embodiment of the method according to the invention, spent catalyst is continuously or gradually discharged from the reaction chamber and optionally replaced by fresh catalyst.

The organic nitro compound used in the method according to the invention can be produced by any method known to the person skilled in the art. Typically the organic nitro compound is produced by nitration of an organic compound, in particular with $NO_x$ and/or nitric acid. The organic compound is selected from the aromatic hydrocarbons benzene and methyl- and/or ethyl-substituted benzenes, in particular toluene. The method according to the invention thus relates to the production of aromatic amines from aromatic nitro compounds, in particular of aromatic polyamines from aromatic polynitro compounds.

According to the invention, the organic nitro compound used according to the method is a nitro aromatic of formula (I)

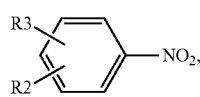

Formula (I)

in which R2 and R3 independently of each other denote hydrogen, methyl or ethyl, wherein R3 can additionally denote $NO_2$.

In the context of the method according to the invention, the organic amino compound is an aromatic amine of formula (II)

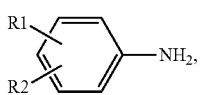

Formula (II)

in which R1 and R2 independently of each other denote hydrogen, methyl or ethyl, wherein R1 can additionally denote $NH_2$.

In the method according to the invention, the hydrogenation can take place at the temperatures and pressures that are familiar to the person skilled in the art for that purpose, preferred temperatures being in the range from 80 to 200° C., in particular 110 to 180° C., and preferred pressures being 5 to 120 bar, in particular 10 to 100 bar. The temperature is measured by means of devices known to the person skilled in the art, such as thermocouples or resistance, semiconductor or infrared thermometers. The pressure is preferably measured using mechanical pressure gauges or electronic pressure sensors.

The present invention also provides a device for producing organic amino compounds, including a reaction chamber for hydrogenation of an organic nitro compound by means of a catalyst and an apparatus for monitoring the reaction course of the hydrogenation by analysing secondary products forming during the hydrogenation, wherein the device is characterised in that the monitoring apparatus is suitable for determining the concentration of gaseous secondary products in the gas phase and is moreover coupled to a control apparatus, which increases the hydrogenating activity of the catalyst if the concentration of the secondary product(s) falls below a predefinable minimum concentration.

A reaction chamber is understood to be a chamber in which the requirements for a reaction in the liquid phase of a nitro aromatic (or intermediates) with hydrogen to form the desired aromatic amine are met. The reaction chamber is located in a technical device for performing chemical reactions, a reactor. Depending on the design, the reaction chamber and reactor can also be identical (in the case of bubble columns for example). The reaction chamber can also include only part of the reactor. If for instance there is a liquid phase only in the lower region of a reactor, the gas phase above it is no longer part of the reaction chamber according to the invention, regardless of the fact that because of the vapour pressure of the nitro aromatic, a—small—proportion of the nitro aromatic enters the gas phase and is reacted there. A reactor can also comprise a plurality of reaction chambers. The reaction chambers can be located in one or in various reactors. Preferred reactors for the method according to the invention are stirred-tank reactors, loop reactors, tubular-flow reactors, bubble columns or jet reactors.

If a plurality of reaction chambers is used, they are preferably connected in series in the method according to the invention, i.e. the product mixture from one reaction chamber is introduced into the subsequent reaction chamber as a reactant mixture. It is possible, although not absolutely necessary, additionally to introduce fresh hydrogen or a mixture of hydrogen and inert gases and optionally fresh catalyst into the downstream reaction chambers. In the method according to the invention the fresh nitro aromatic is typically introduced into only one reaction chamber; this is referred to as the first chamber in the direction of flow of the nitro aromatic and is preferably operated isothermally. All subsequent reaction chambers are loaded only with nitro aromatic that was not reacted in the previous reaction chamber. Accordingly, in the event of complete reaction in the first reaction chamber in the direction of flow of the nitro aromatic, the subsequent reaction chambers are not loaded with nitro aromatic at all.

In an advantageous embodiment of the device according to the invention the monitoring apparatus for determining the concentration of gaseous secondary products is connected to the reaction chamber via an analytical gas line.

In the device according to the invention it can moreover be provided that a condensation apparatus for condensing water vapour is connected upstream of the monitoring apparatus. With this arrangement of equipment, water vapour can be removed from the gas stream prior to the quantitative determination of the secondary product, water vapour possibly making it more difficult to obtain an exact quantitative determination of the secondary product. This is particularly advantageous if the concentration of the gaseous secondary products is determined using an IR spectrometer.

EXAMPLES

FIG. 1 shows a reactor A according to the invention. Molten dinitrotoluene and hydrogen are supplied to reactor A via a reactant line 1 and a hydrogen line 2 respectively. Reactor A contains a mixture of toluylene diamine and water as well as a nickel catalyst, the dinitrotoluene being hydrogenated with hydrogen at a temperature of 130° C. and a pressure of 20 bar.

Part of the reaction mixture, containing inter alia the reactant, the product and the catalyst, is circulated by means of a pump D from reactor A through line sections 8, 9, 3, 5. Line section 9 leads to a cooler F in which the reaction mixture is cooled. From there the cooled reaction mixture is fed via line section 3 to a cross-flow filter E, in which the hydrogenation product, i.e. diaminotoluene ("DNT"), is drawn off via a product line 6. The rest of the reaction mixture is returned to reactor A via line section 5, thus completing the circuit.

The amount of dinitrotoluene melt is adjusted so that the average residence time in reactor A is 2 h. The amount of hydrogen fed to reactor A via the hydrogen line 2 is adjusted so that the pressure in reactor A remains constant.

Reactor A is also connected via a line 7 to a photometric measuring cell G. 1% of the hydrogen feed is continuously discharged from reactor A via line 7 to prevent the accumulation of inerts. At the same time the methane content in the discharged hydrogen is determined quantitatively by means of the photometric measuring cell G. A methane content of approximately 12 mg/kg DNT is determined, for example, which corresponds to the predefined minimum concentration of this secondary product. FIG. 1 illustrates a control apparatus C to which the monitoring apparatus G is coupled and which is configured to increase the hydrogenating activity of the catalyst if the concentration of the gaseous secondary product(s) falls below a predefinable minimum concentration. FIG. 1 also illustrates a condensation apparatus B that is configured to condense water vapor and which is connected upstream of the monitoring apparatus (G).

Figure 2:
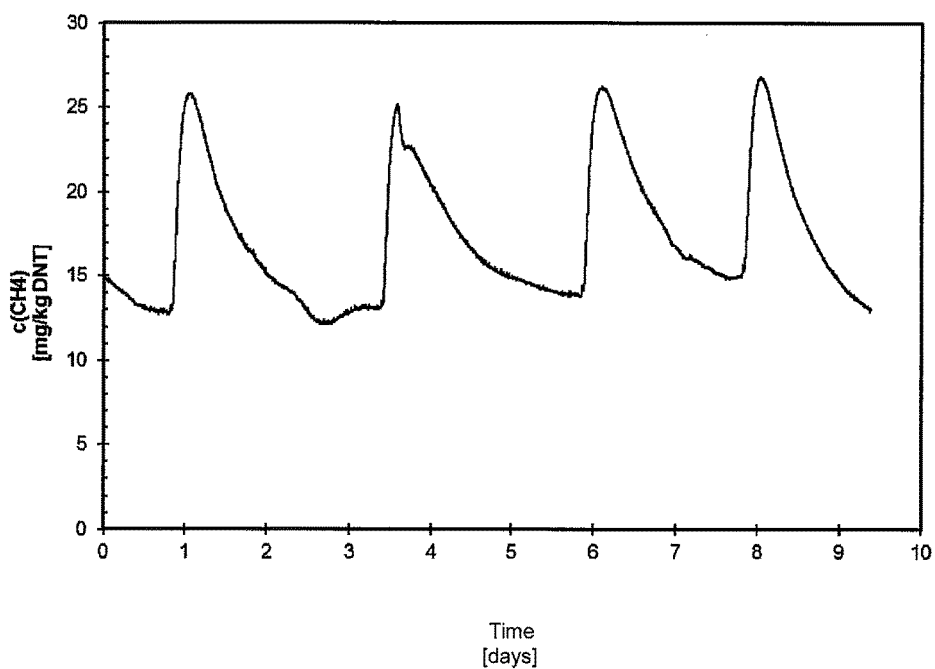
FIG. 2 is a plot of the measured methane concentration in the discharged gas stream versus time.

After one day an amount of catalyst corresponding to 20% of the starting amount is added to the reactor, causing the methane content in the discharged hydrogen to rise to 25 mg/kg DNT. Over a period of approximately 2.5 further days the methane content falls to the initial value due to deactivation of the catalyst. The same amount of catalyst is added again and the methane content rises to 25 mg/kg DNT again accordingly. This progress over time is shown in FIG. 2.

By means of the method according to the invention, the yield of organic amino compound can thus be continuously held at a high level whilst at the same time maintaining a high degree of operational safety by determining the methane content and increasing the hydrogenating activity of the catalyst.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for producing organic amino compounds of formula (II)

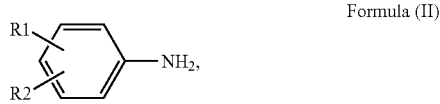

Formula (II)

in which R1 and R2 independently of each other denote hydrogen, methyl or ethyl, wherein R1 can additionally denote $NH_2$, from organic nitro compounds of formula (I)

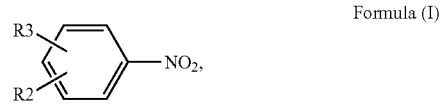

Formula (I)

in which R2 and R3 independently of each other denote hydrogen, methyl or ethyl, wherein R3 can additionally denote $NO_2$, comprising:
  (a) continuously feeding the organic nitro compound and a hydrogen-containing gas stream to a reaction chamber containing a catalyst,
  (b) hydrogenating the organic nitro compound to the organic amino compound in the reaction chamber,
  (c) continuously discharging from the reaction chamber a gas phase comprising 0.1 to 10 wt. % of the hydrogen from the hydrogen-containing gas stream,
  (d) determining a concentration of one or more gaseous secondary products in the continuously discharged gas phase, and
  (e) increasing the catalyst hydrogenating activity if the concentration of the one or more gaseous secondary products falls below a predefined minimum concentration,
  wherein the hydrogenating activity of the catalyst is increased by a method selected from the group consisting of (i) increasing the volumetric flow rate of the hydrogen-containing gas steam to the reaction chamber, (ii) throttling the feed of organic nitro compound to the reaction chamber, (iii) increasing the pressure in the reaction chamber, (iv) increasing the temperature in the reaction chamber, (v) increasing the residence time of the organic nitro compound in the reaction chamber, (vi) adding further catalyst to the reaction chamber, or (vii) a combination thereof.

2. The method according to claim 1, wherein the gaseous secondary product has a boiling point under normal pressure of 200° C. or less.

3. The method according to claim 1, wherein the gaseous secondary product is selected from the group consisting of methane, ammonia, an aliphatic amine which is not one of the organic amino compounds of formula (II), and mixtures thereof, the minimum concentration of the gaseous secondary product being:
  in the case of methane at least 2 mg/kg of organic nitro compound,
  in the case of ammonia at least 2 mg/kg of organic nitro compound, and
  in the case of the aliphatic amine at least 1 mg/kg of organic nitro compound.

4. The method according to claim 1, wherein the concentration of the gaseous secondary product is determined by means of a gas probe or by spectroscopy.

5. The method according to claim 1, wherein water vapor present in the gas phase is removed by condensation before determining the concentration of the gaseous secondary product.

6. The method according to claim 1, wherein the gaseous secondary product is passed through a separating apparatus prior to determining the concentration.

7. The method according to claim 1, wherein spent catalyst is continuously discharged.

8. The method according to claim 1, wherein the organic nitro compound is produced by nitration of an organic compound.

9. The method according to claim 1, wherein the organic nitro compound is dinitrotoluene, which is hydrogenated to toluylene diamine.

10. The method according to claim 1, wherein the hydrogenating is performed at a temperature from 80 to 200° C. and/or the hydrogenating is performed under a pressure from 5 to 120 bar.

11. The method of claim 1, wherein the hydrogenating activity of the catalyst is increased by a method selected from the group consisting of (i) increasing the volumetric flow rate of the hydrogen-containing gas steam to the reaction chamber, (ii) throttling the feed of organic nitro compound to the reaction chamber (iv) increasing the temperature in the reaction chamber, (v) increasing the residence time of the organic nitro compound in the reaction chamber, (vi) adding further catalyst to the reaction chamber, or (vii) a combination thereof.

12. A device configured to produce organic amino compounds, comprising:
(a) a reaction chamber configured to hydrogenate an organic nitro compound by means of a catalyst;
(b) a reactant line configured to continuously feed an organic nitro compound to the reaction chamber, wherein the organic nitro compound is of the formula (I)

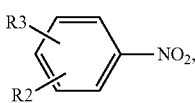
Formula (I)

in which R2 and R3 independently of each other denote hydrogen, methyl or ethyl, wherein R3 can additionally denote $NO_2$
(c) a hydrogen line configured to continuously feed a hydrogen-containing gas stream to the reaction chamber;
(d) a line configured to continuously discharge from the reaction chamber a gas phase comprising 0.1 to 10 wt. % of the hydrogen from the hydrogen-containing gas stream; and
(e) an apparatus configured to monitor the reaction course of the hydrogenation by analysing secondary products forming during the hydrogenation,
wherein the monitoring apparatus is configured to determine a concentration of gaseous secondary product(s) in a gas phase continuously discharged from the reaction chamber, and
wherein the monitoring apparatus is coupled to a control apparatus which is configured to increase hydrogenating activity of the catalyst if the concentration of the gaseous secondary product(s) falls below a predefined minimum concentration by increasing the volumetric flow rate of the hydrogen-containing gas stream to the reaction chamber, by throttling the feed of the organic nitro compound to the reaction chamber, by increasing the pressure in the reaction chamber, by increasing the temperature in the reaction chamber, by increasing the residence time of the organic nitro compound in the reaction chamber, by adding further catalyst to the reaction chamber, or a combination thereof.

13. The device according to claim 12, wherein the monitoring apparatus (G) is connected to the reaction chamber (A) via an analytical gas line.

14. Device according to claim 13, wherein a condensation apparatus for condensing water vapor is connected upstream of the monitoring apparatus (G).

15. The device of claim 12 wherein the control apparatus is configured to increase hydrogenating activity of the catalyst if the concentration of the gaseous secondary product(s) falls below a predefined minimum concentration by increasing the volumetric flow rate of the hydrogen-containing gas stream to the reaction chamber, by throttling the feed of the organic nitro compound to the reaction chamber, by increasing the temperature in the reaction chamber, by increasing the residence time of the organic nitro compound in the reaction chamber, by adding further catalyst to the reaction chamber, or a combination thereof.

* * * * *